US012049442B2

(12) United States Patent
Zhang et al.

(10) Patent No.: US 12,049,442 B2
(45) Date of Patent: Jul. 30, 2024

(54) PREPARATION METHOD OF VINYL ACETATE BY ETHYLENE PROCESS AND DEVICE THEREOF

(71) Applicant: TIANJIN UNIVERSITY, Tianjin (CN)

(72) Inventors: Minhua Zhang, Tianjin (CN); Hao Gong, Tianjin (CN); He Dong, Tianjin (CN); Zhongfeng Geng, Tianjin (CN); Yingzhe Yu, Tianjin (CN)

(73) Assignee: TIANJIN UNIVERSITY, Tianjin (CN)

( * ) Notice: Subject to any disclaimer, the term of this patent is extended or adjusted under 35 U.S.C. 154(b) by 0 days.

(21) Appl. No.: 18/235,136

(22) Filed: Aug. 17, 2023

(65) Prior Publication Data
US 2024/0158333 A1  May 16, 2024

(30) Foreign Application Priority Data
Nov. 16, 2022 (CN) .......................... 202211435930.0

(51) Int. Cl.
*C07C 67/05* (2006.01)
*B01D 53/22* (2006.01)
*B01J 19/00* (2006.01)

(52) U.S. Cl.
CPC .............. *C07C 67/05* (2013.01); *B01D 53/22* (2013.01); *B01J 19/0013* (2013.01); *B01D 2311/25* (2013.01)

(58) Field of Classification Search
CPC . C07C 67/05; C07C 11/04; C07C 5/00; B01J 19/00113; B01D 53/22; B01D 2311/25
See application file for complete search history.

(56) References Cited

U.S. PATENT DOCUMENTS

| 6,118,021 | A  | * | 9/2000  | Gottschlich | .......... | B01J 19/2465 |
|           |    |   |         |             |            | 560/243 |
| 9,636,627 | B2 | * | 5/2017  | Zhang ................. | B01D 53/185 |
| 2023/0312452 | A1 | * | 10/2023 | Zhang ..................... | C07C 67/54 |
|           |    |   |         |             |            | 560/241.1 |
| 2023/0312456 | A1 | * | 10/2023 | Zhang ..................... | C07C 69/15 |
|           |    |   |         |             |            | 560/261 |

FOREIGN PATENT DOCUMENTS

| CN | 102936198 A | * | 2/2013 | ............. C07C 67/05 |
| CN | 112209830 A | * | 1/2021 | ............. C07C 67/05 |
| CN | 112299989 A | * | 2/2021 | ................ B01J 7/00 |
| MY | 125616 A    | * | 8/2006 | ........... C07C 67/055 |

* cited by examiner

*Primary Examiner* — Yate' K Cutliff

(57) ABSTRACT

The present disclosure relates to a process and a device for producing vinyl acetate by an ethylene process. By additionally arranging an ethylene recovery membrane assembly in a vinyl acetate synthesis section, the content of inert components such as nitrogen in a circulating system is controlled, ethylene gas is recovered from non-condensable gas, and a recovery rate of the ethylene reaches 58% or above. By adding sideline extraction at a refined VAC tower in a vinyl acetate refining section, a vinyl acetate product with purity higher than 99.98% is obtained, a mass fraction of acetic acid is less than or equal to 20 ppm, a mass fraction of acetaldehyde is less than or equal to 20 ppm, and a mass fraction of water is less than or equal to 100 ppm. In synthesis and refining processes of the vinyl acetate, a cooling method is adopted.

6 Claims, 4 Drawing Sheets

PREPARATION METHOD OF VINYL ACETATE BY ETHYLENE PROCESS AND DEVICE THEREOF

CROSS-REFERENCE TO RELATED APPLICATION

This application claims priority from the Chinese patent application 2022114359300 filed Nov. 16, 2022, the content of which are incorporated herein in the entirety by reference.

TECHNICAL FIELD

The present disclosure relates to a process for producing vinyl acetate, in particular to a preparation method of vinyl acetate by an ethylene process and device thereof for high-purity products.

BACKGROUND ART

Vinyl acetate (VAc for short) is unsaturated carboxylic ester, its molecular formula is $CH_3COOCH=CH_2$, and it is a vinyl ester compound with high economic value in the chemical industry. Vinyl acetate is colorless and transparent flammable liquid with a slightly pungent smell. It can be soluble completely in a plurality of kinds of organic liquids, and soluble in water partially. Its explosion limit in air ranges from 2.65% to 38% (volume), and it can form an azeotrope with water, methanol, isopropanol and the like.

At present, a technology for producing vinyl acetate by ethylene is a worldwide mainstream process for generating vinyl acetate. China is a major country in consumption and production of ethylene, vinyl acetate and derivative chemicals thereof. For many years, China has not mastered an advanced technology for producing vinyl acetate by ethylene. In the 1970s, China introduced the technology for producing vinyl acetate by the ethylene process from Japan, and established relevant production device. However, at the current stage, a great difference exists between such technological level and an international advanced technology, which restricts the development of polyvinyl alcohol, which is an important downstream product of vinyl acetate, and related industries in China.

*Discussion on the Influence of Trace Impurities on the Production of Polyvinyl Alcohol* has pointed out that impurity components in the production process of polyvinyl alcohol are mainly carried over by reactant vinyl acetate. A polymerization reaction is very sensitive to impurities, and even the presence of trace impurities often causes serious harm to the quality of products. Although the vinyl acetate products produced by the ethylene process are refined, they still contain some impurities, including acetaldehyde, acetic acid, methyl acetate, ethyl acetate and the like. *Polyvinyl Alcohol Production Technology* has pointed out that some of these impurities directly participate in the polymerization reaction, some of them play a role in chain transfer, and some of them play a role in polymerization inhibition. Where, acetaldehyde has a high polymerization inhibition coefficient, and an average degree of polymerization of polyvinyl alcohol decreases as the content of acetaldehyde increases. Acetaldehyde, methyl acetate and acetic acid are chain transfer agents, and the average degree of polymerization of polyvinyl alcohol decreases as the content of these impurities increases. In addition, conjugated double bonds formed after carbonyl of acetaldehyde is ligated to polyvinyl acetate macromolecules of polyvinyl alcohol are one of the important reasons for yellowing of polyvinyl alcohol products. Besides acetaldehyde carried over by the vinyl acetate, a reaction of generating acetaldehyde may also occur in the generation reaction process of polyvinyl alcohol, that is, vinyl acetate may react with water, as well as vinyl acetate may react with solvent methanol to generate acetaldehyde. Trace water contained in vinyl acetate products may also react with the vinyl acetate to generate the acetaldehyde.

The content of impurities in vinyl acetate produced by the ethylene process has been defined by a polyvinyl alcohol production enterprise. It is defined in the In-house Specification Q/SH 1115 104-2018 *Vinyl Acetate* of Sinopec Chongqing SVW Chemical Co., Ltd. that the purity of superior vinyl acetate products is greater than or equal to 99.90% (w), where, the content of acetic acid is less than or equal to 40 ppm, and the content of acetaldehyde is less than or equal to 40 ppm. It is defined in the In-house Specification Q/NSXHB 3003-2020 *Vinyl Acetate for Industrial Use* of INNER MONGOLIA SHUANGXIN ENVIRONMENT-FRIENDLY MATERIAL CO., LTD. that the purity of superior vinyl acetate products is greater than or equal to 99.96% (w), where, the content of acetic acid is less than or equal to 50 ppm, and the content of acetaldehyde is less than or equal to 80 ppm. It is defined in the European Chemicals Report *Joint Assessment of Commodity Chemicals* No. 18 that in vinyl acetate products, the content of acetic acid is less than or equal to 50 ppm, and the content of acetaldehyde is less than or equal to 50 ppm.

A patent ZL 201610553473.3 has disclosed a high-purity vinyl acetate separation system. In the present disclosure, refined vinyl acetate products with the purity of 99.90% (w) or above are obtained, acetic acid in the vinyl acetate products is controlled to be less than 20 mg/kg, and water is controlled to be less than 150 mg/kg.

It is mentioned in *Simulation and Optimization of Improved Process for Vinyl Acetate Production by Gas Phase Ethylene* Process that the purity of vinyl acetate products obtained by an existing process for producing vinyl acetate by an ethylene process (Bayer process) in Sinopec Shanghai Petrochemical Company Limited is 99.80% (w).

In addition, in the process of producing the vinyl acetate by the ethylene process, the conversion per pass of raw materials is low, and a large amount of mixed gas containing unreacted ethylene returns to a reactor to be recycled after being pressurized by a compressor. In order to prevent inert gas, such as nitrogen, hydrogen and methane, in feed gas from being gradually accumulated in process circulating gas that affects the normal reaction, it is necessary to continuously emit part of circulating gas to a flare for incineration. Since the circulating gas contains much ethylene, if it is directly fed to be incinerated, not only are economic losses caused, but also a large amount of greenhouse gas is generated to pollute the environment, aggravating the environmental protection burden on enterprises. The water content in the vinyl acetate products is strictly limited, materials should be cooled in order to ensure phase splitting and dehydrating effects. At present, plate heat exchangers have been used in existing processes, featuring complete countercurrent heat exchange by utilizing circulating water.

In conclusion, the processes for producing the vinyl acetate by the ethylene process at the present stage mainly have the following problems:

(1) the emission load of three wastes (waste water, waste gas, and industrial residues) is large, non-condensable gas emitted in a synthesis section contains much ethylene, and if it is directly incinerated, not only are economic losses caused, but also a large amount of greenhouse gas is generated to pollute the environment.

(2) The product purity hardly meets the purity requirements of superior vinyl acetate products required by each enterprise. The content of acetic acid, acetaldehyde and other impurities is high, so that the production requirements of downstream products are hardly met. The vinyl acetate products have high requirements for the water content.

(3) The plate exchangers mainly have the defects of easy leakage, frequent overhaul, long sealing periphery and the like. Since the plate exchangers are frequently used, materials are prone to leakage, resulting in environmental pollution, and even work and production standstill.

SUMMARY

The present disclosure relates to a preparation method of vinyl acetate by an ethylene process, in particular to a preparation method of vinyl acetate by an ethylene process for high-purity products and a device thereof. The present disclosure aims at providing a novel process for producing vinyl acetate by an ethylene process for high-purity products, so as to obtain high-purity vinyl acetate products which cannot realize in similar devices, and meanwhile reduce emissions of three wastes and avoid material leakage, so as to protect the environment.

In order to realize the above objectives of the present disclosure, the technical solution of the present disclosure is as follows:

A preparation method of vinyl acetate by an ethylene process, includes the following methods including:

(a) a step of feeding non-condensable gas of an absorption tower gas-liquid separation tank into an ethylene recovery membrane assembly, and recovering ethylene from the non-condensable gas through membrane separation;

(b) a step of feeding vinyl acetate containing a polymerization inhibitor and high-boiling-point impurities into a refined VAC tower, and drawing from a side of the refined VAC tower, to obtain a high-purity VAC product; and (c) a step of allowing overhead vapour of an acetic acid tower and overhead vapour of a crude VAC tower to enter a distillation phase splitting tank after passing through an overhead condenser and a condensate cooler adopting circulating water series cooling and a tail gas condenser for cooling with chilled water respectively.

In the step (a), the ethylene recovery membrane assembly is additionally arranged between the absorption tower gas-liquid separation tank and a flare.

In the step (b), a side-draw stream is additionally added at third to seventh theoretical plates on an upper portion of the refined VAC tower.

In the step (c), original respective and independent cooling of the overhead condenser and the condensate cooler is improved into a cooling method for cooling with circulating water in series respectively on the top of the acetic acid tower and the top of the crude VAC tower.

A device for realizing the step (a) in the preparation method of vinyl acetate by the ethylene process includes: an ethylene recovery membrane assembly includes an aggregator and membrane equipment; a stream at an overhead outlet of an absorption tower gas-liquid separation tank is divided into two streams connected with an inlet of the ethylene recovery membrane assembly and a cooling side inlet of a refined gas heat exchanger respectively; and an outlet of the ethylene recovery membrane assembly is connected with a flare inlet and an inlet of a gas recovery compressor.

A device for realizing the step (b) includes: an overhead outlet of a refined VAC tower is connected with a cooling side inlet of a refined VAC tower condenser, and a cooling side outlet of the refined VAC tower condenser is connected with a cooling side inlet of a refined VAC tower condensate cooler; a cooling side outlet of the refined VAC tower condensate cooler is connected with a refined VAC tower reflux tank; circulating water enters from a heating side inlet of the refined VAC tower condensate cooler, a heating side outlet of the refined VAC tower condensate cooler is connected with a heating side inlet of the refined VAC tower condenser, and the circulating water exits from a heating side outlet of the refined VAC tower condenser; a side outlet of the refined VAC tower is connected with a cooling side inlet of a VAC product condenser, and a cooling side outlet of the VAC product condenser is connected with a VAC product tank; chilled water enters from a heating side inlet of the VAC product condenser, and exits from a heating side outlet of the VAC product condenser; and a tower kettle outlet of the refined VAC tower is connected with an upper end inlet of an acetic acid tower.

A device for realizing the step (c) includes: an overhead outlet of an acetic acid tower is connected with a cooling side inlet of an acetic acid tower condenser, and a cooling side outlet of the acetic acid tower condenser is connected with a cooling side inlet of an acetic acid condenser cooler and a cooling side inlet of an acetic acid tower tail gas condenser; a cooling side outlet of the acetic acid tower tail gas condenser is connected with an inlet of a gas recovery compressor and an inlet of an acetic acid tower distillation phase splitting tank, respectively; a cooling side outlet of the acetic acid tower condensate cooler (208) is connected with the inlet of the acetic acid tower distillation phase splitting tank; a circulating water inlet is connected with a heating side inlet of the acetic acid condenser cooler, a heating side outlet of the acetic acid condenser cooler is connected with a heating side inlet of the acetic acid tower condenser, and a heating side outlet of the acetic acid tower condenser is connected with a circulating water outlet; and a chilled water inlet is connected with a heating side inlet of the acetic acid tower tail gas condenser, and a heating side outlet of the acetic acid tower tail gas condenser is connected with a chilled water outlet.

A device for realizing the step (c), an overhead outlet of a crude VAC tower and an overhead outlet of a dehydrating tower are both connected with a cooling side inlet of a crude VAC tower condenser, and a cooling side outlet of the crude VAC tower condenser is connected with a cooling side inlet of a crude VAC tower condensate cooler and a cooling side inlet of a crude VAC tower tail gas condenser; a cooling side outlet of the crude VAC tower tail gas condenser is connected with an inlet of a gas recovery compressor and an inlet of a crude VAC tower distillation phase splitting tank, respectively; a cooling side outlet of the crude VAC tower condensate cooler is connected with the inlet of the crude VAC tower distillation phase splitting tank; a chilled water inlet is connected with a heating side inlet of the crude VAC tower tail gas condenser, and a heating side outlet of the crude VAC tower tail gas condenser is connected with a chilled water outlet; and a circulating water inlet is connected with a heating side inlet of the crude VAC tower condensate cooler, a heating side outlet of the crude VAC tower condensate cooler is connected with a heating side inlet of the crude VAC tower condenser, and a heating side outlet of the crude VAC tower condenser is connected with a circulating water outlet.

The preparation method of vinyl acetate by the ethylene process according to the present disclosure further includes the following technical solution that refined gas from a synthesis and refining system is fed at the bottoms of the acetic acid tower and an aldehydo-ester concentrating tower; one part of tower bottoms of the acetic acid tower is fed to a synthesis section, and the other part thereof and the refined gas from the synthesis and refining system return to a lower portion of the acetic acid tower after passing through an acetic tower reboiler; and one part of tower bottoms of the aldehydo-ester concentrating tower and distillate of an extractive distillation tower phase splitting tank return to the top of the crude VAC tower together, and the other part thereof and the refined gas from the synthesis and refining system return to a lower portion of the aldehydo-ester concentrating tower after passing through an aldehydo-ester concentrating tower reboiler.

Details are as follows:

(1) Synthesis Process of Vinyl Acetate

Synthesis of the vinyl acetate mainly includes two parts of a synthesis reaction and gas refining. The vinyl acetate is synthesized mainly by taking ethylene, oxygen and acetic acid as raw materials, synthesizing the vinyl acetate through a fixed-bed catalytic oxidation reaction, separating circulating gas from reaction liquid, recycling feed gas such as ethylene, discharging gaseous reaction products such as carbon dioxide and inert gas, and supplying the reaction liquid to a downstream rectifying section.

Fresh acetic acid enters a tower top of an acetic acid evaporator from the outside of a boundary region. Fresh ethylene from the outside of the boundary region is mixed with circulating ethylene at an outlet of a circulating gas compressor. Feed flow of the fresh ethylene is adjusted according to an inlet pressure of a synthesis reactor. Circulating gas mixed with the fresh ethylene enters a tower kettle of the acetic acid evaporator after being in coupled heat transfer with reaction gas emitted out of the synthesis reactor through a second reaction gas cooler. Acetic acid in the tower kettle of the acetic acid evaporator is fed out, and a small amount of the acetic acid, serving as residues, is discharged to an acetic acid recovery unit in the rectifying section, so as to prevent accumulation of tar and other high-boiling-point impurities in a distilled acetic acid circulating system, and most of the acetic acid circulates to a middle of the acetic acid evaporator after being heated by low-pressure vapour through an acetic acid heater. High-temperature distilled acetic acid from a tower kettle of the acetic acid tower also enters a middle of the acetic acid evaporator. Fresh acetic acid is sprayed to a top of the acetic acid evaporator, and is in countercurrent contact with ascending gas flow in the acetic acid evaporator, so as to complete purification on evaporated acetic acid. Circulating gas saturated by acetic acid is led out of the top of the acetic acid evaporator. An overhead temperature of the acetic acid evaporator is controlled at a set value by adjusting the heating vapour quantity of the acetic acid heater, and thus the acetic acid content in the circulating gas is controlled within a range required by the process.

The circulating gas emitted out of the top of the acetic acid evaporator and saturated by the acetic acid enters a first reaction gas cooler to be in coupled heat transfer with the reaction gas emitted out of the synthesis reactor, and after being heated, the circulating gas is heated to a specified temperature by medium-pressure vapour through a circulating ethylene preheater according to different operating stages of the device. The gas is mixed with oxygen in an oxygen mixer, and the oxygen concentration in the circulating gas is controlled within the range required by the process by adjusting the oxygen addition amount. An atomized potassium acetate solution as a cocatalyst is added to the gas emitted out of the oxygen mixer, so as to supplement the cocatalyst lost in the reactor. The circulating gas supplemented with potassium acetate enters a catalyst bed for synthesizing the vinyl acetate from a top of the synthesis reactor for a catalytic reaction. The synthesis reactor is a tubular fixed bed reactor with pressurized water for heat removal, and ethylene, oxygen and acetic acid in reaction feed gas undergo a chemical reaction on a surface of a catalyst, converting them into the vinyl acetate. Additionally, a partial side reaction also occurs during this process. The pressurized water is located on a shell side of the synthesis reactor, and thermo-syphon natural circulation is formed by heated vaporization on a shell pass of the synthesis reactor and vapour-liquid separation in a reactor vapour pocket, so as to remove reaction heat. Generated secondary vapour enters a vapour pipe network at a corresponding grade to be used for the process.

Reacted gas is discharged from a bottom of the synthesis reactor, which contains a large amount of unconverted ethylene and acetic acid, carbon dioxide, water, oxygen, nitrogen and the like besides containing target product vinyl acetate, and these products should be separated by condensing and cooling, washing and other operations.

Reaction gas discharged from the reactor firstly exchanges heat with circulating feed gas in the first reaction gas cooler and the second reaction gas cooler, so as to recover heat brought therefrom. Reaction gas from the second reaction gas cooler enters a first gas separation tower, gas discharged from a tower top is partially condensed by a first gas separation tower condenser and a first gas separation tower aftercooler, and uncondensed gas enters a second gas separation tower. Condensate enters a first gas separation tower phase splitting tank after being further cooled by a first gas separation tower condensate cooler. Circulating water is adopted in the overhead condenser of the first gas separation tower, the tail gas condenser and the condensate cooler as a cooling medium. The condensate separated from the first gas separation tower phase splitting tank enters a water phase receiving tank and a degassing tank respectively. An organic phase separated from the first gas separation tower phase splitting tank is fed back to the tower top of the first gas separation tower, so as to ensure that no acetic acid is contained in overhead gas of the first gas separation tower.

Gas discharged from the first gas separation tower aftercooler still contains a large quantity of condensable components, which will be fed to the second gas separation tower for further separation. The second gas separation tower includes an upper section and a lower section, the lower section is a reaction liquid circulating cooling section, and the upper section is an acetic acid washing section. One part of tower bottoms of the second gas separation tower, serving as reaction liquid, is continuously drawn to be fed to the degassing tank, and the other part thereof is cooled by circulating water and chilled water in a second gas separation tower first cooler and a second gas separation tower second cooler in sequence, and then fed back to the second gas separation tower to be in countercurrent contact with ascending gas, so that most of condensable components therein are condensed. Distilled acetic acid from a tower kettle of the acetic acid tower enters the upper section of the second gas separation tower after being cooled by a circulating ethylene heat exchanger and a second gas separation tower acetic acid cooler to leach the ascending gas in the tower, so that vinyl acetate is further recovered from the gas, and gas from a top of the second gas separation tower basically does not contain vinyl acetate and other condensable components. The gas converges with refined gas after exchanging heat with the distilled acetic acid from the tower kettle of the acetic acid tower by the circulating ethylene heat exchanger, and after the gas is pressurized by being compressed by the circulating gas compressor, a small part of the gas is extracted as side stream gas to remove carbon dioxide and other inert components, so as to ensure no decrease in the ethylene concentration in the circulating gas caused by accumulation of the inert components, thereby realizing a smooth synthesis reaction. The remaining circulating gas circulates to the acetic acid evaporator after being mixed with fresh ethylene from the outside of the boundary region.

Tail gas from a degassing tank tail gas condenser in the rectifying section, tail gas from the acetic acid tower, tail gas from the crude VAC tower and tail gas from the aldehydo-ester concentrating tower are mixed with the side stream gas from the circulating gas compressor after being pressurized by a gas recovery compressor, and mixed gas enters a washing tower after exchanging heat with refined gas by a refined gas heat exchanger for washing to remove acid. The gas recovery compressor is a two-stage liquid ring compressor, diluted acetic acid is adopted as a sealing working solution, tower bottoms of the washing tower are adopted as a supplementary working solution, and the drained working solution is fed to the degassing tank.

The washing tower includes three sections of a lower section, a middle section and a top, wherein the lower section is a circulating cooling section, most of tower bottoms are cooled by a washing tower cooler and then fed back to the lower section of the washing tower for circulating cooling, and the remaining tower bottoms are fed out to be used as a working solution of the gas recovery compressor; cold rectified acetic acid from the second acetic acid separation tower acetic acid cooler enters the middle section of the washing tower, so as to remove organic condensable components such as vinyl acetate from the ascending gas; and desalted water enters the top of the washing tower after being cooled by a pure water cooler to leach the ascending gas flow in the tower, so that acetic acid is removed therefrom.

Gas discharged from the top of the washing tower enters an absorption tower, and carbon dioxide is removed therefrom by chemical absorption of a potassium carbonate aqueous solution, so as to control the carbon dioxide content in the circulating gas. Refined gas discharged from a top of the absorption tower enters an absorption tower gas-liquid separation tank after being condensed by an absorption tower condenser. Condensate in the tank enters a tower kettle of a desorption tower; and part of non-condensable gas is fed to the ethylene recovery membrane assembly in order to control the content of inert components such as nitrogen in the circulating system, recovered ethylene returns to the recovered gas compressor, and emitted tail gas is fed to the flare to be incinerated. The remaining non-condensable gas enters the refined gas heat exchanger to exchange heat with side stream gas and recovered gas. Most of heated refined gas enters the circulating gas compressor after being mixed with the circulating gas; a small part thereof is directly mixed with tail gas from the ethylene recovery membrane assembly to be fed to the flare for incineration, so as to control the ethane content in the circulating gas; and a small amount thereof is fed to the acetic acid tower and the aldehydo-ester concentrating tower in the rectifying section.

Absorption liquid (rich liquid) drained by a tower kettle of the absorption tower enters a feed flash tank of the desorption tower after exchanging heat with lean liquid by a lean and rich liquid heat exchanger, ethylene-containing gas flashed off at a reduced pressure enters the degassing tank, a flashed liquid phase enters the desorption tower, and potassium bicarbonate is decomposed by heating under reduced pressure, so as to release carbon dioxide. Discharged water-containing carbon dioxide gas enters a desorption tower gas-liquid separation tank after being condensed by a desorption tower condenser, gaseous carbon dioxide is continuously emitted out of the boundary region, and condensate is fed to the absorption tower; and a potassium carbonate solution (lean liquid) drained by a tower kettle of the desorption tower is fed out by an absorption liquid circulating pump. The product enters a top of the absorption tower after exchanging heat with the rich liquid by the lean and rich liquid heat exchanger and being cooled by a potash lye cooler, so as to control the content of carbon dioxide in the refined gas.

(2) Refining Process of Vinyl Acetate

Refining of the vinyl acetate mainly includes treatment of synthesis reaction liquid and tower bottoms of the acetic acid evaporator. Materials from the synthesis section contain vinyl acetate, acetic acid, water and other low-boiling-point and high-boiling-point impurities. The acetic acid is separated from the materials by a rectifying method to be recycled in the synthesis section; the vinyl acetate is refined into high-purity products as products of the device for sales or self use; and separated-out high-boiling-point waste liquid and low-boiling-point waste liquid are fed out of the boundary region for incineration.

Reaction liquid from the tower kettles of the first gas separation tower and the second gas separation tower for vinyl acetate, sealing liquid from the gas recovery compressor, part of an aqueous phase from the first gas separation tower phase splitting tank and recovered acetic acid from an acetic acid recovery tower in the rectifying section enter the degassing tank.

After a gas phase discharged from the degassing tank is condensed by the degassing tank condenser and the degassing tank tail gas condenser, condensate returns to the degassing tank, and a gas phase enters the gas recovery compressor in the synthesis section. Degassed reaction liquid is fed to the acetic acid tower for feeding.

Vinyl acetate is separated from acetic acid in the acetic acid tower through azeotropy of vinyl acetate and water. Acetic acid not containing vinyl acetate and other light components obtained from the tower kettle is fed back to the synthesis section by the rectified acetic acid pump as rectified acetic acid, to be used for feeding of the acetic acid evaporator and acetic acid leaching of the second gas separation tower and the washing tower.

An overhead distillate from the acetic acid tower is a mixture of vinyl acetate and water that are close to azeotropic composition, and after the mixture is condensed by the acetic acid tower condenser and the acetic acid tower tail gas condenser, tail gas and ethylene-containing tail gas discharged from each tower in the rectifying section return to the gas recovery compressor in the synthesis section. Condensate enters the acetic acid tower distillation phase splitting tank after being further cooled by the acetic acid tower condensate cooler, condensate from the acetic acid tower tail gas condenser also enters the acetic acid tower distillation phase splitting tank, and a separated-out aqueous phase automatically enters the water phase receiving tank; an oil phase partially refluxes, and the remaining part is fed to the crude VAC tower for feeding. The same stream of circulating water is fed to the overhead condenser and the acetic acid tower condensate cooler as a cooling medium. Part of a liquid-phase material is drawn out of an ethyl acetate enrichment region in the acetic acid tower and fed to the extracting and rectifying tower for separation of ethyl acetate and recovery of vinyl acetate and acetic acid from the side-drawn distillate. In addition, refined gas from the synthesis and refining system is blown from the tower bottom, thereby achieving polymerization inhibition.

Water contained in crude VAC is removed through azeotropy of vinyl acetate and water while removing light impurities from the crude VAC tower, and water-free vinyl acetate is obtained in the tower kettle and fed to the refined VAC tower for feeding. After overhead vapour from the crude VAC tower is condensed by the crude VAC tower condenser and the crude VAC tower tail gas condenser, tail gas is fed to the gas recovery compressor after converging with ethylene-containing tail gas from each tower. Condensate enters the crude VAC tower distillation phase splitting tank after being further cooled by the crude VAC tower condensate cooler, condensate from the tail gas condenser also enters the crude VAC tower distillation phase splitting tank, a separated-out aqueous phase automatically flows to the water phase receiving tank, an oil phase partially refluxes, and the remaining part is fed to the aldehydo-ester concentrating tower for concentrating the light impurities. The same stream of circulating water is fed to the overhead of crude VAC tower condenser and the crude VAC tower condensate cooler as the cooling medium.

Tower bottoms in the refined VAC tower are vinyl acetate containing a polymerization inhibitor and high-boiling-point impurities, and are fed to the acetic acid tower for feeding. High-purity vinyl acetate products are distilled out of the tower top. Refined VAC vapour distilled out of the tower top of the refined VAC tower enters the refined VAC tower reflux tank after being condensed and cooled by the refined VAC tower condenser and the refined VAC tower condensate cooler, one part refluxes, and the other part enters the acetic acid tower. A side-drawn distillate from the refined VAC tower is fed to a VAC product region after being cooled by the VAC product condenser. The same stream of circulating water is fed to the overhead of refined VAC tower condenser and the refined VAC tower condenser cooler as the cooling medium.

A side-drawn stream rich in ethyl acetate from the acetic acid tower enters a middle of the extracting and rectifying tower. Acetic acid, serving as an extractant, is added from an upper portion of the extracting and rectifying tower, and vinyl acetate is separated from ethyl acetate by an extracting and rectifying technology due to strong interaction between the acetic acid and the trace ethyl acetate in the vinyl acetate.

Tower bottoms of the extracting and rectifying tower are acetic acid rich in ethyl acetate and fed to the ethyl acetate tower. Azeotrope vapour of vinyl acetate and water with ethyl acetate removed is obtained from the tower top of the extracting and rectifying tower, and enters the extracting and rectifying tower phase splitting tank after being condensed and cooled by the extracting and rectifying rower condenser and the extracting and rectifying tower condensate cooler, a separated-out aqueous phase automatically flows to the water phase receiving tank, an oil phase partially refluxes, and the remaining part, serving as recovered vinyl acetate, is fed back to the crude VAC tower for feeding. The same stream of circulating water is fed to the overhead of extracting and rectifying tower condenser and the extracting and rectifying tower condensate cooler as the cooling medium.

Ethyl acetate is separated from acetic acid in the ethyl acetate tower. Water-containing acetic acid with ethyl acetate removed is obtained in the tower kettle, one part, serving as an extractant, returns to the upper section of the extracting and rectifying tower, and the other part is fed back to the acetic acid tower for feeding. Vapour rich in ethyl acetate distilled out of the tower top of the ethyl acetate tower enters the ethyl acetate tower phase splitting tank after being condensed and cooled by the ethyl acetate tower condenser and the ethyl acetate tower condensate cooler, a separated-out aqueous phase enters the ethyl acetate tower reflux tank, and refluxes completely; and an oil phase is drawn and fed out of the boundary region for incineration. The same stream of circulating water is fed to the overhead of ethyl acetate tower condenser and the ethyl acetate tower condensate cooler as the cooling medium.

The aldehydo-ester concentrating tower operates under pressure, and tower bottoms rich in VAC are fed back to the top of the crude VAC tower for feeding. After overhead gas from the aldehydo-ester concentrating tower is condensed by the aldehydo-ester concentrating tower condenser, tail gas is fed to the recovered gas compressor unit after converging with ethylene-containing tail gas from each tower. One part of condensate refluxes through the reflux tank, and the other part thereof is drawn and fed to the acetaldehyde tower for feeding.

Tower bottoms of the acetaldehyde tower, serving as low-boiling-point waste liquid, are fed out of the boundary region for incineration. Overhead gas of the acetaldehyde tower enters the acetaldehyde tower reflux tank after being condensed by the overhead of acetaldehyde tower condenser, one part of the overhead gas refluxes, and the other part thereof, serving as byproduct acetaldehyde, is fed to a tank region.

An aqueous phase obtained by the first gas separation tower phase splitting tank, the acetic acid tower distillation phase splitting tank, the crude VAC tower distillation phase splitting tank and the extracting and rectifying tower phase splitting tank enters the water phase receiving tank, and enters the dehydrating tower after exchanging heat with kettle water of the dehydrating tower by a dehydrating tower feed preheater. Water-containing vinyl acetate vapour is obtained on the tower top, and fed to the crude VAC tower condenser for condensing. Tower bottoms are process waste water, and are subjected to sewage treatment after heat is recovered by the dehydrating tower feed preheater.

Tar-containing acetic acid discharged from the acetic acid evaporator in the synthesis section enters an acetic acid recovery tower feed tank, flashed-out ethylene-containing gas is fed to the degassing tank, and residual liquid enters the acetic acid recovery tower.

The acetic acid recovery tower implements distillation under reduced pressure, acetic acid vapour is obtained on the tower top, and enters an acetic acid recovery tower reflux tank after being condensed by an acetic acid recovery tower condenser, one part refluxes, and the other part, serving as recovered acetic acid, is fed to the degassing tank. Tower bottoms are high-boiling-point waste liquid and are fed out of the boundary region.

In the preparation method and the device, the polymerization inhibitor is added to the stream containing vinyl acetate and equipment, so as to prevent vinyl acetate from self-polymerization.

Vapour condensed water generated by medium-pressure and low-pressure vapour users in a device region enter a vapour condensate flash tank to be flashed at a pressure of 0.1 MPa. Secondary vapour is used as a heating heat source of the crude VAC tower and the aldehydo-ester concentrating tower, and the part that is insufficient for heating is supplemented by low-pressure vapour; and flashed condensed water is fed out by a condensate flash tank discharge pump, part of heat is recovered therefrom by a vapour pocket water supplementing heat exchanger, or the condensed water directly enters a low-pressure condensed water tank with the heat exchanger only serving as a channel.

The condensed water enters the low-pressure condensed water tank for operation under reduced pressure, generated secondary vapour is used as a heating source for the refined VAC tower reboiler, and the part that is insufficient for heating is supplemented by low-pressure vapour. Condensed water generated after heat exchange enters a condensed water tank, and then is fed back to the low-pressure condensed water tank.

Condensed water in the low-pressure condensed water tank is fed out by a low-pressure condensed water pump, one part is fed to an oxygen extractor to serve as water supplement of a reactor vapour pocket, and the other part is fed out of the boundary region.

The present disclosure has the following advantages and beneficial effects:

1. The present disclosure relates to the novel process for producing the vinyl acetate by the ethylene process for the high-purity products, which has the advantages that the ethylene recovery membrane assembly is additionally arranged between the absorption tower gas-liquid separation tank and the flare, and the ethylene recovery membrane assembly includes an aggregator and membrane equipment. The ethylene recovery membrane assembly is used for controlling the content of inert components such as nitrogen in the circulating system and recovering ethylene gas from the non-condensable gas, so as to reduce losses caused by the fact that raw material ethylene is directly fed to be incinerated in the non-condensable gas. Most ethylene can be recovered from vent gas by the ethylene recovery membrane assembly, and the recovery rate of the ethylene can reach 58% or above. Emissions of three wastes are reduced, so that environmental protection is realized. Meanwhile, the aggregator in the membrane assembly has two effects that firstly, gas flows from bottom to top, and a demister in the aggregator can prevent water in the stream from flowing into the membrane equipment. Secondly, electric trace heating is arranged on a pipeline led out of the aggregator for heating, so that gas enters the membrane equipment after being overheated by 3-5° C., thereby preventing condensation caused by the fact that saturated gas directly makes contact with the membrane equipment.

2. The novel process for producing the vinyl acetate by the ethylene process for the high-purity products according to the present disclosure has the advantages that one side-draw stream is additionally added at the third to seventh theoretical plates on the upper portion of the refined VAC tower, vinyl acetate products with the purity higher than 99.98% can be obtained, a mass fraction of acetic acid is less than or equal to 20 ppm, a mass fraction of acetaldehyde is less than or equal to 20 ppm, and a mass fraction of water is less than or equal to 100 ppm.

3. The novel process for producing the vinyl acetate by the ethylene process for the high-purity products according to the present disclosure has the advantages that in synthesis and refining processes of the vinyl acetate, a cooling method is adopted, which includes the overhead condenser and the condensate cooler adopting circulating water series cooling and the tail gas condenser for cooling with both the circulating water and chilled water in parallel. This method allows for the cascade utilization of cooling capacity of the circulating water during a heat exchange process, as well as energy conservation; and meanwhile, the problems such as material leakage caused by a plate heat exchanger are avoided, and the volume of the heat exchanger is reduced.

4. The novel process for producing the vinyl acetate by the ethylene process for the high-purity products according to the present disclosure has the advantages that by feeding refined gas from the synthesis and refining system into the bottoms of the acetic acid tower and the aldehydo-ester concentrating tower, the polymerization inhibition effect is achieved.

5. The novel process for producing the vinyl acetate by the ethylene process for the high-purity products according to the present disclosure has the advantages that the vapour condensed water generated by the medium-pressure and low-pressure vapour users in the device region is flashed under a certain pressure, the obtained secondary vapour is used as the heating source of the crude VAC tower and the aldehydo-ester concentrating tower, the flashed condensed water and the secondary vapour condensed water are subjected to reduced pressure flashing again, and the generated secondary vapour is used as the heating source of the refined VAC tower. The condensed water obtained after heat exchanger can be fed to the oxygen extractor to serve as the water supplement of the reactor vapour pocket. By means of the above measures, vapour consumption of the system is effectively reduced, and the production cost is reduced.

Figure 1:
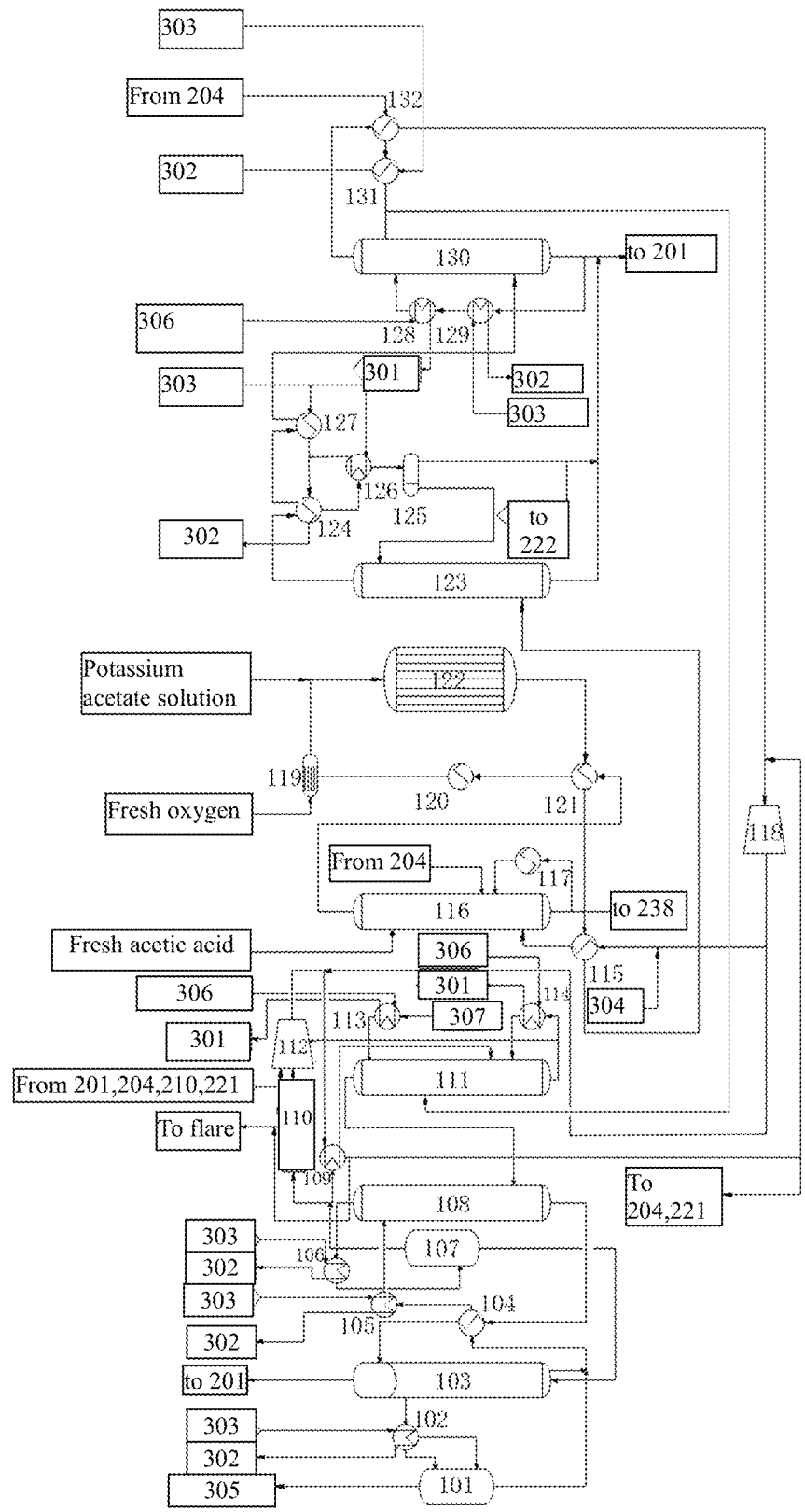
FIG. 1 is a flowchart of an energy-saving preparation method and device for synthesizing vinyl acetate by an ethylene process for high-purity products according to the present disclosure.

Where, the names and numbers of the components are shown in the figures: desorption tower gas-liquid separation tank 101, desorption tower condenser 102, desorption tower 103, lean and rich liquid heat exchanger 104, potash lye cooler 105, absorption tower condenser 106, absorption tower gas-liquid separation tank 107, absorption tower 108, refined gas heat exchanger 109, ethylene recovery membrane assembly 110, washing tower 111, gas recovery compressor 112, pure water cooler 113, washing tower cooler 114, second reaction gas cooler 115, acetic acid evaporator 116, acetic acid heater 117, circulating gas compressor 118, oxygen mixer 119, circulating ethylene preheater 120, first reaction gas cooler 121, synthesis reactor 122, first gas separation tower 123, first gas separation tower condenser 124, first gas separation tower phase splitting tank 125, first gas separation tower condensate cooler 126, first gas separation tower aftercooler 127, second gas separation tower second cooler 128, second gas separation tower first cooler 129, second gas separation tower 130, second gas separation tower acetic acid cooler 131, circulating ethylene heat exchanger 132, degassing tank 201, degassing tank condenser 202, degassing tank tail gas condenser 203, acetic acid tower 204, acetic acid tower reboiler 205, acetic acid tower condenser 206, acetic acid tower distillation phase splitting tank 207, acetic acid tower condensate cooler 208, acetic acid tower tail gas condenser 209, crude VAC tower 210, refined VAC tower 211, crude VAC tower reboiler 212, crude VAC tower condenser 213, refined VAC tower condenser 214, VAC product condenser 215, crude VAC tower distillation phase splitting tank 216, crude VAC tower condensate cooler 217, refined VAC tower condensate cooler 218, refined VAC tower reflux tank 219, crude VAC tower tail gas condenser 220, aldehydo-ester concentrating tower 221, water phase receiving tank 222, aldehydo-ester concentrating tower reboiler 223, aldehydo-ester concentrating tower condenser 224, aldehydo-ester concentrating tower reflux tank 225, acetaldehyde tower 226, dehydrating tower feed preheater 227, acetaldehyde tower reboiler 228, acetaldehyde tower condenser 229, acetaldehyde tower reflux tank 230, extracting and rectifying tower 231, dehydrating tower (232), extracting and rectifying tower reboiler 233, dehydrating tower reboiler 234, extracting and rectifying tower condenser 235, extracting and rectifying tower condensate cooler 236, extracting and rectifying tower phase splitting tank 237, acetic acid recovery tower feed tank 238, ethyl acetate tower 239, ethyl acetate tower condenser 240, ethyl acetate tower phase splitting tank 241, ethyl acetate tower reflux tank 242, acetic acid recovery tower 243, ethyl acetate condensate cooler 244, acetic acid recovery tower condenser 245, and acetic acid recovery tower reflux tank 246;

301: chilled water outflow, 302: circulating water outflow, 303: circulating water inflow, 304: fresh ethylene; 305: feed carbon dioxide out of boundary region, 306: chilled water inflow, 307: desalted water, 308: VAC product, 309: feed low-boiling-point waste liquid out of boundary region, 310: feed high-boiling-point waste liquid out of boundary region, 311: acetaldehyde product, 312: waste water treatment.

DETAILED DESCRIPTION OF THE PRESENT DISCLOSURE

The present disclosure is further described in detail below with reference to the accompanying drawings and specific embodiments. The following embodiments are merely descriptive and not restrictive, and do not limit the scope of protection of the present disclosure.

The specific implementation process of the method of the present application is described with the specific embodiments below.

Embodiment

As shown in FIG. 1, a flowchart of an energy-saving preparation method and device for synthesizing vinyl acetate by an ethylene process for high-purity products is shown as follows:

A feed quantity of raw material acetic acid is 179000 kg/h. Fresh acetic acid enters a tower top of an acetic acid evaporator 116 from the outside of a boundary region. Fresh ethylene from the outside of the boundary region is mixed with circulating ethylene at an outlet of a circulating gas compressor 118, with a feed quantity of 8700 kg/h. Circulating gas mixed with the fresh ethylene enters a tower kettle of the acetic acid evaporator 116 after being in coupled heat transfer with reaction gas discharged from the synthesis reactor 122 through a second reaction gas cooler 115. Acetic acid in the tower kettle of the acetic acid evaporator 116 is fed out, a small amount of the acetic acid, serving as residues, is discharged to an acetic acid recovery unit in a rectifying section, and most of the acetic acid circulates to a middle of the acetic acid evaporator 116 after being heated by low-pressure vapour through an acetic acid heater 117. High-temperature distilled acetic acid from a tower kettle of an acetic acid tower 204 also enters the middle of the acetic acid evaporator 116. Fresh acetic acid is sprayed to the top of the acetic acid evaporator 116. Circulating gas saturated by acetic acid is led out of the top of the acetic acid evaporator 116. An overhead temperature of the acetic acid evaporator 116 is 123° C., a tower kettle temperature thereof is 109° C., and an operating pressure is 0.85 MPa.

Circulating gas discharged from the top of the acetic acid evaporator 116 and saturated by acetic acid enters a first reaction gas cooler 121 to be in coupled heat transfer with reaction gas discharged from the synthesis reactor 122, and the circulating gas is heated to a specified temperature by a circulating ethylene preheater 120. The gas is mixed with oxygen in an oxygen mixer 119. An atomized potassium acetate solution as a cocatalyst is added to the gas discharged from the oxygen mixer 119, and enters a catalyst bed for synthesizing the vinyl acetate from a top of the synthesis reactor 122. An inlet temperature of the oxygen mixer 119 is 156° C., an outlet temperature thereof is 155° C., and an operating pressure is 0.83 MPa. An inlet temperature of the synthesis reactor 122 is 155° C., an outlet temperature thereof is 160° C., and an operating pressure is 0.80 MPa.

Reacted gas, discharged from a bottom of the synthesis reactor 122, is firstly exchanged heat with circulating feed gas in the first reaction gas cooler 121 and the reaction gas second cooler 115. Reaction gas from the second reaction gas cooler 115 enters a first gas separation tower 123, gas discharged from a tower top is partially condensed by a first gas separation tower condenser 124 and a first gas separation tower aftercooler 127, and uncondensed gas enters a second gas separation tower 130. Condensate enters a first gas separation tower phase splitting tank 125 after being further cooled by a first gas separation tower condensate cooler 126. The condensate separated from the first gas separation tower phase splitting tank 125 enters a water phase receiving tank 222 and a degassing tank 201 respectively. An organic phase separated from the first gas separation tower phase splitting tank 125 is fed back to the tower top of the first gas separation tower 123. An overhead temperature of the acetic acid evaporator 123 is 81° C., a tower kettle temperature thereof is 115° C., and an operating pressure is 0.65 MPa.

Gas discharged from the first gas separation tower aftercooler 127 is fed to the second gas separation tower 130. One part of tower bottoms of the second gas separation tower 130, serving as reaction liquid, is continuously drawn to be fed to the degassing tank 201, and the other part thereof is fed back to the second gas separation tower 130 after being cooled by a second gas separation tower first cooler 129 and a second gas separation tower second cooler 128 in sequence. Distilled acetic acid from the tower kettle of the acetic acid tower 204 enters an upper section of the second gas separation tower 130 after being cooled by a circulating ethylene heat exchanger 132 and a second gas separation tower acetic acid cooler 131. The gas converges with refined gas after exchanging heat with the distilled acetic acid from the tower kettle of the acetic acid tower 204 by the circulating ethylene heat exchanger 132, and after the gas is pressurized by being compressed by the circulating gas compressor 118, a small part of the gas is extracted as side stream gas to remove carbon dioxide and other inert components. The remaining circulating gas circulates to the acetic acid evaporator 116 after being mixed with fresh ethylene from the outside of the boundary region. An overhead temperature of the second gas separation tower 130 is 30° C., a tower kettle temperature thereof is 48° C., and an operating pressure is 0.59 MPa.

Tail gas from a degassing tank tail gas condenser 203 in the rectifying section, tail gas from the acetic acid tower, tail gas from the crude VAC tower and tail gas from the aldehydo-ester concentrating tower are mixed with the side stream gas from the circulating gas compressor 118 after being pressurized by a gas recovery compressor 112, and mixed gas enters a washing tower 111 after exchanging heat with the refined gas by a refined gas heat exchanger 109 for washing to remove acid. Most of tower bottoms of the washing tower 111 are fed back to a lower section of the washing tower 111 for circulating cooling after being cooled by a washing tower cooler 114, and the remaining tower bottoms are fed out and used as a working solution of the gas recovery compressor 112; cold rectified acetic acid from the second acetic acid separation tower acetic acid cooler 131 enters a middle section of the washing tower 111; and desalted water enters a top of the washing tower 111 after being cooled by a pure water cooler 113. A tower top temperature of the washing tower 111 is 35° C., a tower kettle temperature thereof is 43° C., and an operating pressure is 0.82 MPa.

Figure 3:
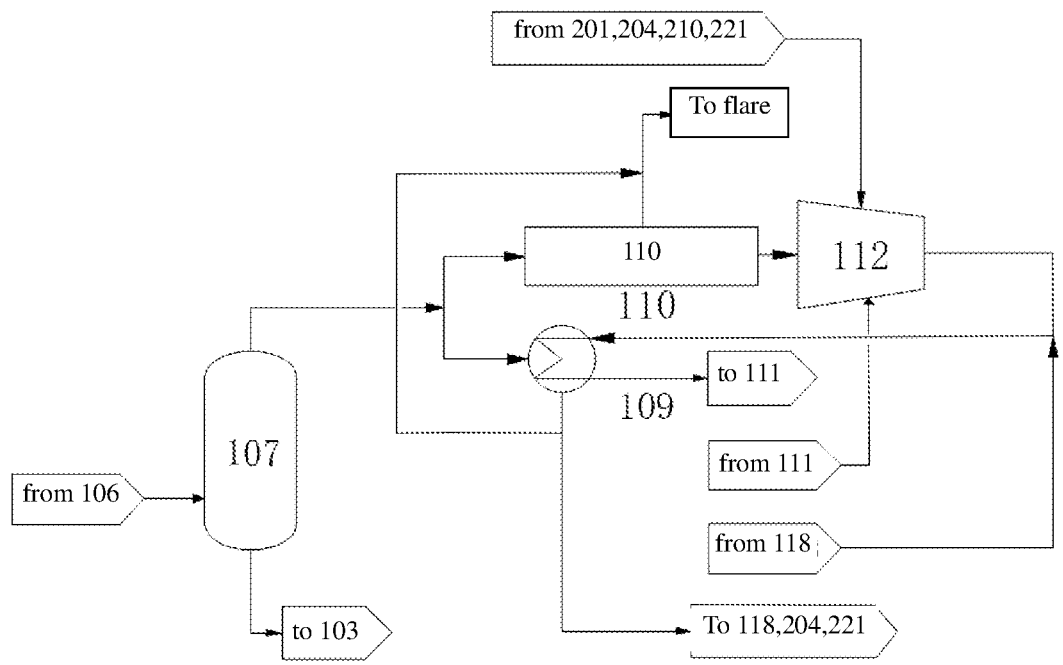
FIG. 3 is a flowchart of a preparation method and a device at an ethylene recovery membrane assembly.

Gas discharged from the tower top of the washing tower 111 enters an absorption tower 108. Refined gas discharged from a top of the absorption tower 108 enters an absorption tower gas-liquid separation tank 107 after being condensed by an absorption tower condenser 106. Condensate in the tank enters a tower kettle of a desorption tower 103. As shown in FIG. 3, a flowchart of a preparation method and a device at an ethylene recovery membrane assembly is shown as follows: part of non-condensable gas is fed to the ethylene recovery membrane assembly 110, recovered ethylene returns to the gas recovery compressor 112, and emitted tail gas is fed to a flare to be incinerated. The remaining non-condensable gas enters the refined gas heat exchanger 109. Most of heated refined gas enters the circulating gas compressor 118 after being mixed with the circulating gas; a small part thereof is directly mixed with tail gas from the ethylene recovery membrane assembly 110 to be fed to the flare for incineration; and a small amount thereof is fed to the acetic acid tower 204 and an aldehydo-ester concentrating tower 221 in the rectifying section. An overhead temperature of the washing tower 108 is 75° C., a tower kettle temperature thereof is 80° C., and an operating pressure is 0.82 MPa.

Absorption liquid drained by a tower kettle of the absorption tower 108 enters a feed flash tank of the desorption tower 103 by a lean and rich liquid heat exchanger 104, ethylene-containing gas flashed off under reduced pressure enters the degassing tank (201), and a flashed liquid phase enters the desorption tower 103. Emitted water-containing carbon dioxide gas enters a desorption tower gas-liquid separation tank 101 after being condensed by a desorption tower condenser 102, gaseous carbon dioxide is continuously discharged from the boundary region, and condensate is fed to the absorption tower 108; and a potassium carbonate solution drained by a tower kettle of the desorption tower 103 is fed out by an absorption liquid circulating pump. The product passes through the lean and rich liquid heat exchanger 104, and enters the top of the absorption tower 108 after being cooled by a potash lye cooler 105. An overhead temperature of the desorption tower 103 is 105° C., a tower kettle temperature thereof is 115° C., and an operating pressure is 0.05 MPa.

Figure 2:
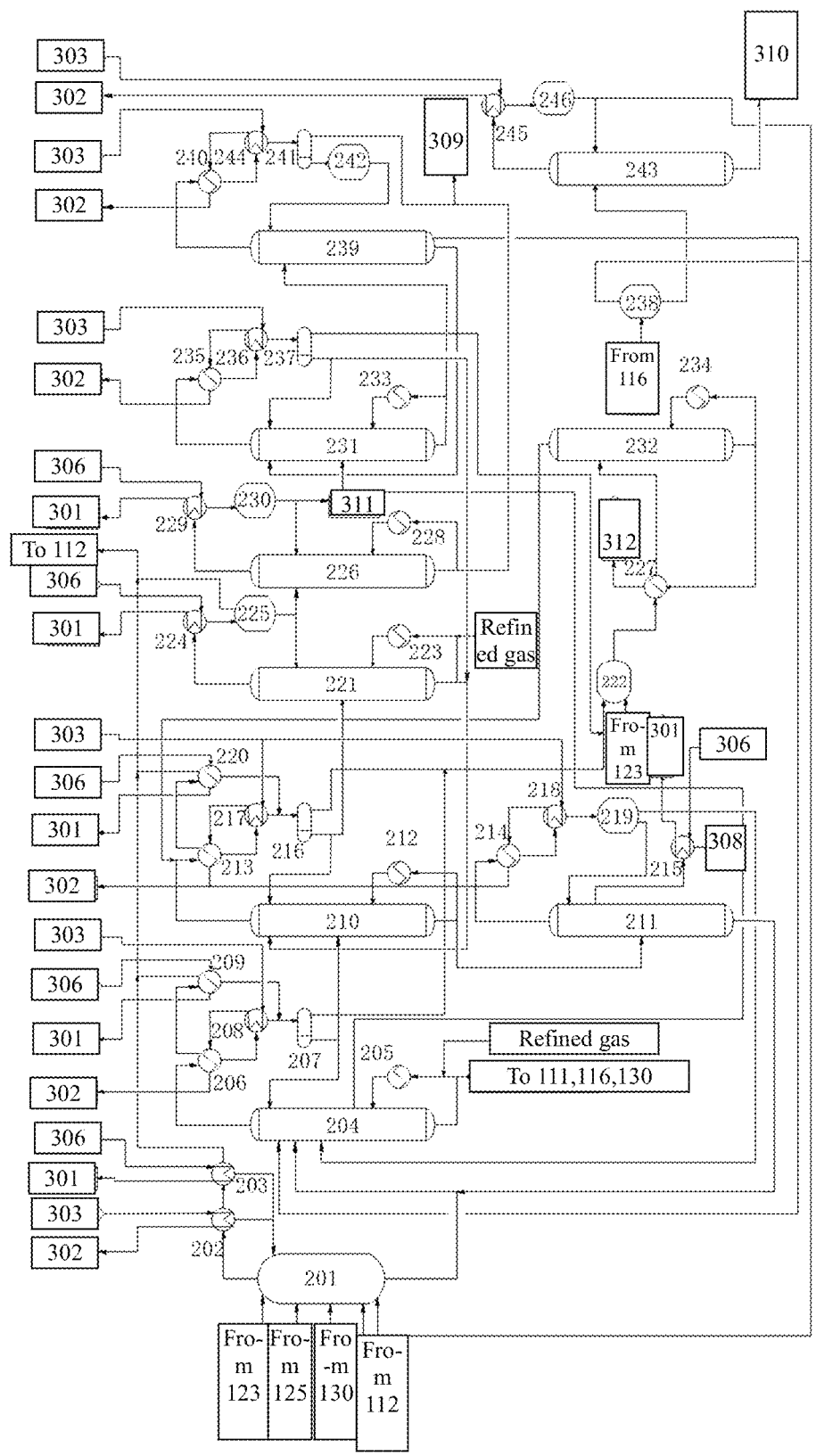
FIG. 2 is a flowchart of an energy-saving preparation method and device for refining vinyl acetate by an ethylene process for high-purity products according to the present disclosure.

As shown in FIG. 2, a flowchart of an energy-saving preparation method and device for refining vinyl acetate by an ethylene process for high-purity products is shown as follows: Reaction liquid from the tower kettles of the first gas separation tower 123 and the second gas separation tower 130 for vinyl acetate, sealing liquid from the gas recovery compressor 112, part of an aqueous phase from the first gas separation tower phase splitting tank 125 and recovered acetic acid from an acetic acid recovery tower 243 in the rectifying section enter the degassing tank 201. After a gas phase discharged from the degassing tank 201 is condensed by the degassing tank condenser 202 and the degassing tank tail gas condenser 203, condensate returns to the degassing tank 201, and a gas phase enters the gas recovery compressor 112 in the synthesis section. Degassed reaction liquid is fed to the acetic acid tower 204 for feeding.

Figure 5:
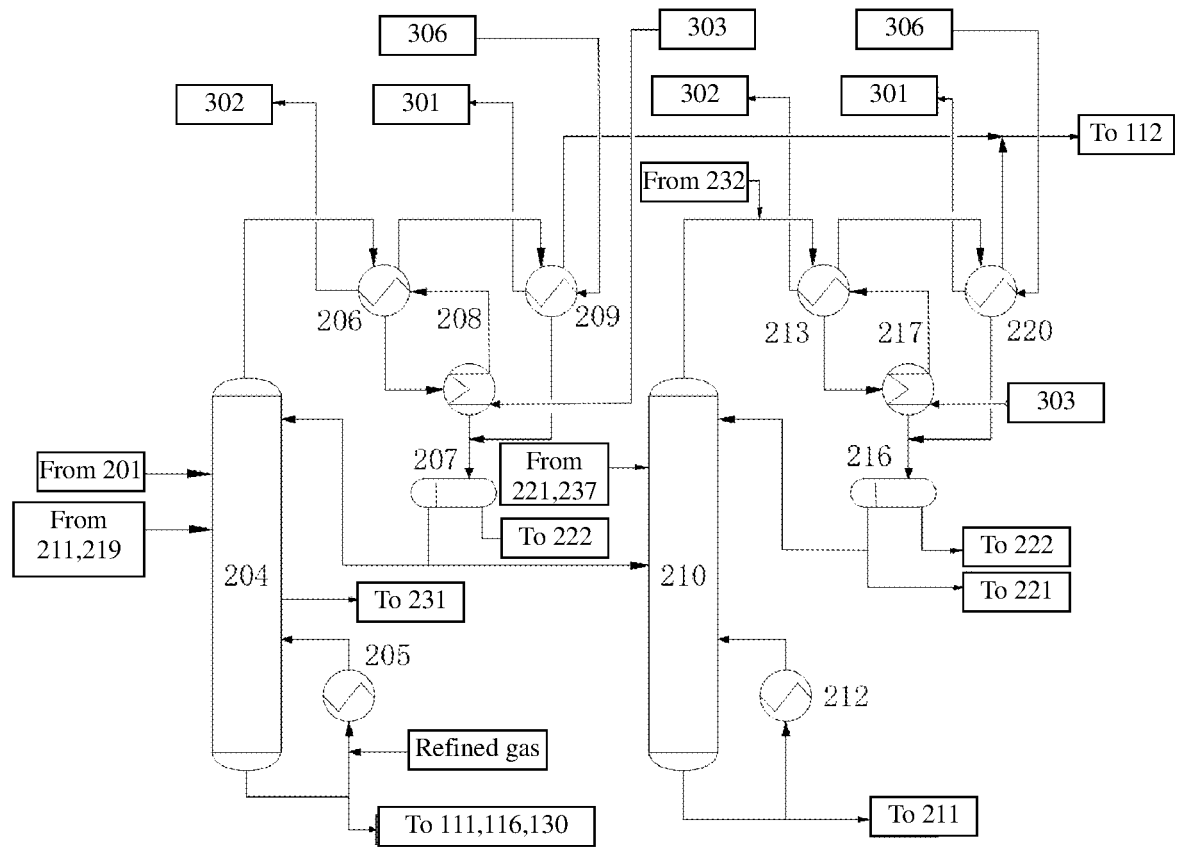
FIG. 5 is a flowchart of a preparation method and a device at an acetic acid tower and a crude VAC tower.

As shown in FIG. 5, a flowchart of a preparation method and a device at the acetic acid tower and the crude VAC tower is shown as follows: acetic acid not containing vinyl acetate and other light components obtained from the tower kettle of the acetic acid tower 204, serving as rectified acetic acid, is fed back to the synthesis section by a rectified acetic acid pump to be used for feeding of the acetic acid evaporator 116 and acetic acid leaching of the second gas separation tower 130 and the washing tower 111. After an overhead distillate of the acetic acid tower 204 is condensed by the acetic tower condenser 206 and the acetic acid tower tail gas condenser 209, tail gas and ethylene-containing tail gas discharged from each tower in the rectifying section return to the gas recovery compressor 112 in the synthesis section. Condensate enters the acetic acid tower distillation phase splitting tank 207 after being further cooled by the acetic acid tower condensate cooler 208, condensate from the acetic acid tower tail gas condenser 209 also enters the acetic acid tower distillation phase splitting tank 207, and a separated-out aqueous phase automatically flows to the water phase receiving tank 222; an oil phase partially refluxes, and the remaining part is fed to the crude VAC tower 210 for feeding. Part of a liquid-phase material is drawn out of an ethyl acetate enrichment region in the acetic acid tower 204 and fed to the extracting and rectifying tower 231 for separation of ethyl acetate and recovery of vinyl acetate and acetic acid from the side-drawn distillate. An overhead temperature of the acetic acid tower 204 is 69° C., a tower kettle temperature thereof is 125° C., and an operating pressure is 0.011 MPa.

As shown in FIG. 5, the flowchart of the preparation method and the device at the acetic acid tower and the crude VAC tower is shown as follows: water-free vinyl acetate is obtained in a tower kettle of the crude VAC tower 210 and fed to a refined VAC tower 211 for feeding. After overhead vapour from the crude VAC tower 210 is condensed by the crude VAC tower condenser 213 and the crude VAC tower tail gas condenser 220, tail gas is fed to the gas recovery compressor 112 after converging with ethylene-containing tail gas from each tower. Condensate enters the crude VAC tower distillation phase splitting tank 219 after being further cooled by the crude VAC tower condensate cooler 217, condensate from the tail gas condenser also enters the crude VAC tower distillation phase splitting tank 219, a separated-out aqueous phase automatically flows to the water phase receiving tank 222, an oil phase partially refluxes, and the remaining part is fed to the aldehydo-ester concentrating tower 221 for concentrating the light impurities. An overhead temperature of the crude VAC tower 210 is 70.7° C., a tower kettle temperature thereof is 81° C., and an operating pressure is 0.011 MPa.

Figure 4:
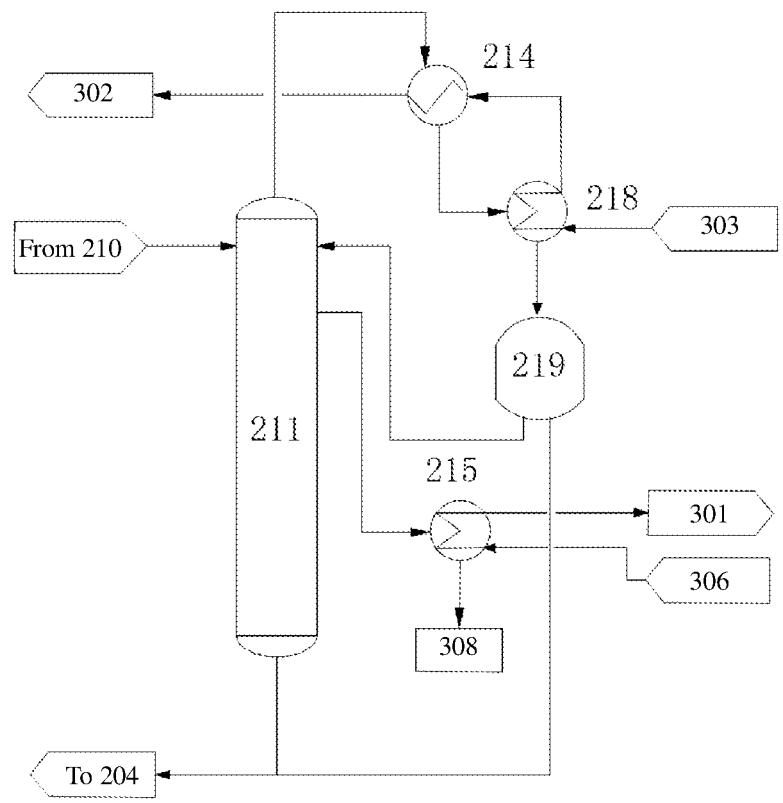
FIG. 4 is a flowchart of a preparation method and a device at a refined VAC tower.

As shown in FIG. 4, a flowchart of a preparation method and a device at the refined VAC tower is shown as follows: tower bottoms in the refined VAC tower 211 are vinyl acetate containing a polymerization inhibitor and high-boiling-point impurities, which are fed to the acetic acid tower 204 for feeding. High-purity vinyl acetate products are distilled out of the tower top. Refined VAC vapour distilled out of the tower top of the refined VAC tower 211 enters the refined VAC tower reflux tank 219 after being condensed and cooled by the refined VAC tower condenser 214 and the refined VAC tower condensate cooler 218, one part refluxes, and the other part enters the acetic acid tower 204. A side-drawn distillate from the refined VAC tower 211 is fed to a VAC product region after being cooled by the VAC product condenser 215. An overhead temperature of the refined VAC tower 211 is 73° C., a tower kettle temperature thereof is 74° C., and an operating pressure is 0.003 MPa.

A side-drawn stream rich in ethyl acetate from the acetic acid tower 204 enters a middle of the extracting and rectifying tower 231. Acetic acid, serving as an extractant, is added from an upper portion of the extracting and rectifying tower 231. Tower bottoms of the extracting and rectifying tower 231 are acetic acid rich in ethyl acetate and fed to an ethyl acetate tower 239. Azeotrope vapour of vinyl acetate and water with ethyl acetate removed is obtained from the tower top of the extracting and rectifying tower 231, and enters the extracting and rectifying tower phase splitting tank 237 after being condensed and cooled by the extracting and rectifying rower condenser 235 and the extracting and rectifying tower condensate cooler 236, a separated-out aqueous phase automatically flows to the water phase receiving tank 222, an oil phase partially refluxes, and the remaining part, serving as recovered vinyl acetate, is fed back to the crude VAC tower 210 for feeding. An overhead temperature of the extracting and rectifying tower 231 is 68° C., a tower kettle temperature thereof is 109° C., and an operating pressure is 0.011 MPa.

Water-containing acetic acid with ethyl acetate removed is obtained in the tower kettle of the ethyl acetate tower 239, one part, serving as an extractant, returns to the upper section of the extracting and rectifying tower 231, and the other part is fed back to the acetic acid tower 204 for feeding. Vapour rich in ethyl acetate distilled out of a tower top of the ethyl acetate tower 239 enters the ethyl acetate tower phase splitting tank 241 after being condensed and cooled by an ethyl acetate tower condenser 240 and an ethyl acetate tower condensate cooler 244, a separated-out aqueous phase enters an ethyl acetate tower reflux tank 242, and refluxes completely; and an oil phase is drawn and fed out of the boundary region for incineration. An overhead temperature of the ethyl acetate tower 239 is 100° C., a tower kettle temperature thereof is 110° C., and an operating pressure is 0.011 MPa.

A material rich in VAC in a tower kettle of the aldehydo-ester concentrating tower 221 is fed back to the top of the crude VAC tower 210 for feeding, after overhead gas is condensed by an aldehydo-ester concentrating tower condenser 224, tail gas enters the gas recovery compressor 112 after converging with ethylene-containing tail gas from each tower. One part of condensate refluxes through the reflux tank, and the other part thereof is drawn and fed to an acetaldehyde tower 226 for feeding. An overhead temperature of the aldehydo-ester concentrating tower 221 is 38.8° C., a tower kettle temperature thereof is 81.3° ° C., and an operating pressure is 0.055 MPa.

Tower bottoms of the acetaldehyde tower 226, serving as low-boiling-point waste liquid, are fed out of the boundary region for incineration, overhead gas enters a acetaldehyde tower reflux tank 230 after being condensed by an overhead of acetaldehyde tower condenser 229, one part refluxes, and the other part, serving as byproduct acetaldehyde, is fed to a tank field. An overhead temperature of the acetaldehyde tower 226 is 23.6° C., a tower kettle temperature thereof is 58° C., and an operating pressure is 0.011 MPa.

An aqueous phase obtained by the first gas separation tower phase splitting tank (125), the acetic acid tower distillation phase splitting tank 207, the crude VAC tower distillation phase splitting tank 216 and the extracting and rectifying tower phase splitting tank 237 enters the water phase receiving tank 222, and enters the dehydrating tower 232 after exchanging heat with kettle water of the dehydrating tower by the dehydrating tower feed preheater 227. Water-containing vinyl acetate vapour is obtained on the tower top, and fed to the crude VAC tower condenser 213 for condensing. Tower bottoms are process waste water, and are subjected to sewage treatment after heat is recovered by the dehydrating tower feed preheater 227. An overhead temperature of the dehydrating tower 232 is 90° C., a tower kettle temperature thereof is 103° C., and an operating pressure is 0.011 MPa.

Tar-containing acetic acid discharged from the acetic acid evaporator 116 in the synthesis section enters the acetic acid recovery tower feed tank 238, flashed-out ethylene-containing gas is fed to the degassing tank 201, and residual liquid enters the acetic acid recovery tower 243. Acetic acid vapour is obtained on a tower top of the acetic acid recovery tower 243, and enters an acetic acid recovery tower reflux tank 246 after being condensed by an acetic acid recovery tower condenser 245, one part refluxes, and the other part, serving as recovered acetic acid, is fed to the degassing tank 201. Tower bottoms are high-boiling-point waste liquid and are fed out of the boundary region. An overhead temperature of the acetic acid recovery tower 243 is 89.6° C., a tower kettle temperature thereof is 102.5° C., and an operating pressure is 0.011 MPa.

The problems, mainly existing in an existing process for producing the vinyl acetate by the ethylene process, finally solved by the embodiment include:
(1) Most ethylene can be recovered from vent gas by the ethylene recovery membrane assembly, and the recovery rate of the ethylene can reach 58% or above. Emissions of three wastes are reduced, so that environmental protection can be realized.
(2) After side-draw distillate from the refined VAC tower is cooled, vinyl acetate products with a mass fraction of 99.98% can be obtained, a mass fraction of acetic acid is less than or equal to 20 ppm, a mass fraction of acetaldehyde is less than or equal to 20 ppm, and a mass fraction of water is less than or equal to 100 ppm.
(3) By adopting a cooling manner of the overhead condenser and the condensate cooler adopting circulating water series cooling and a tail gas condenser for cooling with both the circulating water and chilled water in parallel in synthesis and refining processes of the vinyl acetate, the cascade utilization of cooling capacity of the circulating water during the heat exchange process is achieved, energy is saved, meanwhile, the problems such as material leakage caused by a plate heat exchanger are avoided, and the volume of the heat exchanger is reduced.

Although the present disclosure has been described with reference to the specific embodiments and drawings, the present disclosure is not expected to be limited to the specific form here. On the contrary, the scope of the present disclosure is only limited by the appended claims. In addition, although independent features may be included in different claims, these features may be advantageously combined, and the inclusion in different claims does not mean that the combination of features is not feasible and/or advantageous. References to "first", "second," etc., do not exclude plurals.

What is claimed is:

1. A preparation method of vinyl acetate, comprising:
    (a) a step of feeding non-condensable gas of an absorption tower gas-liquid separation tank into an ethylene recovery membrane assembly, and recovering ethylene from the non-condensable gas through membrane separation; the ethylene recovery membrane assembly (110) comprises an aggregator and membrane equipment; the ethylene recovery membrane assembly (110) is used for controlling the content of inert components including nitrogen in the circulating system and recovering ethylene gas from the non-condensable gas, so as to reduce losses caused by the fact that raw material ethylene is directly fed to be incinerated in the non-condensable gas; the aggregator in the membrane assembly has two effects that firstly, gas flows from bottom to top, and a demister in the aggregator can prevent water in the stream from flowing into the membrane equipment; secondly, electric trace heating is arranged on a pipeline led out of the aggregator for heating, so that gas enters the membrane equipment after being overheated by 3-5° C., thereby preventing condensation caused by the fact that saturated gas directly makes contact with the membrane equipment;
    (b) a step of feeding vinyl acetate containing a polymerization inhibitor and high-boiling-point impurities into a refined VAC tower, and drawing from a side of the refined VAC tower, to obtain a high-purity VAC product; and
    (c) a step of allowing overhead vapour of an acetic acid tower and overhead vapour of a crude VAC tower to enter a distillation phase splitting tank after passing through an overhead condenser and a condensate cooler adopting circulating water series cooling and a tail gas condenser for cooling with chilled water respectively.

2. The preparation method of vinyl acetate according to claim 1, wherein in the step (a), the ethylene recovery membrane assembly (110) is additionally arranged between an absorption tower gas-liquid separation tank (107) and a flare.

3. The preparation method of vinyl acetate according to claim 1, wherein in the step (b), a side-draw stream is additionally added at third to seventh theoretical plates on an upper portion of the refined VAC tower.

4. The preparation method of vinyl acetate according to claim 1, wherein in the step (c), original respective and independent cooling of the overhead condenser and the condensate cooler is improved into a cooling method for cooling with the circulating water in series respectively on a top of the acetic acid tower (204) and a top of the crude VAC tower (210).

5. The preparation method of vinyl acetate according to claim 1, wherein refined gas from a synthesis and refining system is fed at bottoms of the acetic acid tower (204) and an aldehydo-ester concentrating tower (221); one part of tower bottoms of the acetic acid tower (204) is fed to a synthesis section, and the other part thereof and the refined gas from the synthesis and refining system return to a lower portion of the acetic acid tower (204) after passing through an acetic tower reboiler (205); and one part of tower bottoms of the aldehydo-ester concentrating tower (221) and distillate of an extractive distillation tower phase splitting tank (237) return to a top of the crude VAC tower (210), and the other part thereof and the refined gas from the synthesis and refining system return to a lower portion of the aldehydo-ester concentrating tower (221) after passing through an aldehydo-ester concentrating tower reboiler (223).

6. The preparation method of vinyl acetate according to claim 1, wherein the preparation method is realized by a device comprising an ethylene recovery membrane assembly (110); and the ethylene recovery membrane assembly (110) comprises an aggregator and membrane equipment; a stream at an overhead outlet of an absorption tower gas-liquid separation tank (107) is divided into two streams connected with an inlet of the ethylene recovery membrane assembly (110) and a cooling side inlet of a refined gas heat exchanger (109) respectively; and an outlet of the ethylene recovery membrane assembly (110) is connected with a flare inlet and an inlet of a gas recovery compressor (112), respectively; wherein an overhead outlet of a refined VAC tower (211) is connected with a cooling side inlet of a refined VAC tower condenser (214), and a cooling side outlet of the refined VAC tower condenser (214) is connected with a cooling side inlet of a refined VAC tower condensate cooler (218); a cooling side outlet of the refined VAC tower condensate cooler (218) is connected with a refined VAC tower reflux tank (219); circulating water enters from a heating side inlet of the refined VAC tower condensate cooler (218), a heating side outlet of the refined VAC tower condensate cooler (218) is connected with a heating side inlet of the refined VAC tower condenser (214), and the circulating water exits from a heating side outlet of the refined VAC tower condenser (214); a side outlet of the refined VAC tower (211) is connected with a cooling side inlet of a VAC product condenser (215), and a cooling side outlet of the VAC product condenser (215) is connected with a VAC product tank; chilled water enters from a heating side inlet of the VAC product condenser (215), and exits from a heating side outlet of the VAC product condenser (215); and a tower kettle outlet of the refined VAC tower (211) is connected with an upper end inlet of the acetic acid tower (204);

wherein an overhead outlet of an acetic acid tower (204) is connected with a cooling side inlet of an acetic acid tower condenser (206), and a cooling side outlet of the acetic acid tower condenser (206) is connected with a cooling side inlet of an acetic acid condenser cooler (208) and a cooling side inlet of an acetic acid tower tail gas condenser (209); a cooling side outlet of the acetic acid tower tail gas condenser (209) is connected with an inlet of a gas recovery compressor (112) and an inlet of an acetic acid tower distillation phase splitting tank (207); a cooling side outlet of the acetic acid tower condensate cooler (208) is connected with the inlet of the acetic acid tower distillation phase splitting tank (207); a circulating water inlet is connected with a heating side inlet of the acetic acid condenser cooler (208), a heating side outlet of the acetic acid condenser cooler (208) is connected with a heating side inlet of the acetic acid tower condenser (206), and a heating side outlet of the acetic acid tower condenser (206) is connected with a circulating water outlet; and a chilled water inlet is connected with a heating side inlet of the acetic acid tower tail gas condenser (209), and a heating side outlet of the acetic acid tower tail gas condenser (209) is connected with a chilled water outlet;

wherein an overhead outlet of a crude VAC tower (210) and an overhead outlet of a dehydrating tower (232) are both connected with a cooling side inlet of a crude VAC tower condenser (213), and a cooling side outlet of the crude VAC tower condenser (213) is connected with a cooling side inlet of a crude VAC tower condensate cooler (217) and a cooling side inlet of a crude VAC tower tail gas condenser (220); a cooling side outlet of the crude VAC tower tail gas condenser (220) is connected with an inlet of a gas recovery compressor (112) and an inlet of a crude VAC tower distillation phase splitting tank (216); a cooling side outlet of the crude VAC tower condensate cooler (217) is connected with the inlet of the crude VAC tower distillation phase splitting tank (216); a chilled water inlet is connected with a heating side inlet of the crude VAC tower tail gas condenser (220), and a heating side outlet of the crude VAC tower tail gas condenser (220) is connected with a chilled water outlet; and a circulating water inlet is connected with a heating side inlet of the crude VAC tower condensate cooler (217), a heating side outlet of the crude VAC tower condensate cooler (217) is connected with a heating side inlet of the crude VAC tower condenser (213), and a heating side outlet of the crude VAC tower condenser (213) is connected with a circulating water outlet.

\* \* \* \* \*